United States Patent [19]

Beach et al.

[11] 4,394,322

[45] Jul. 19, 1983

[54] GROUP VA YLIDES AND PROCESS FOR PREPARING SAME

[75] Inventors: David L. Beach, Gibsonia; James J. Harrison, Glenshaw, both of Pa.

[73] Assignee: Gulf Research & Development Company, Pittsburgh, Pa.

[21] Appl. No.: 210,283

[22] Filed: Nov. 25, 1980

Related U.S. Application Data

[63] Continuation-in-part of Ser. No. 179,079, Aug. 18, 1980, Pat. No. 4,293,502, and a continuation of Ser. No. 179,080, Aug. 18, 1980, and a continuation of Ser. No. 179,076, Aug. 18, 1980, Pat. No. 4,293,727, and a continuation of Ser. No. 179,005, Aug. 18, 1980, Pat. No. 4,310,716.

[51] Int. Cl.$^3$ .......................... C07F 9/72; C07F 9/74; C07F 9/90; C07F 9/50
[52] U.S. Cl. .................................. 260/440; 260/446; 568/13; 568/14; 568/15
[58] Field of Search ................... 260/440, 446; 568/13, 568/14, 15

[56] References Cited

U.S. PATENT DOCUMENTS 2,998,416  8/1961  Mendel ............................... 260/93.7
3,686,159  8/1972  Bauer et al. ........................ 260/94.9

OTHER PUBLICATIONS

Kosolapoff et al., Organic Phosphorus Compounds, vol. 3, pp. 97-108, (1972).
Doak et al., Organometallic Compounds of Arsenic, Antimony & Bismuth, John Wiley & Sons, N. Y., pp. 225-227, 343-344, (1970).
Ramirez et al., J. Organic Chem. 22, pp. 41-45, (1957).
Hauser, J. Organic Chem. 27, 43-46, (1962).
Ahrland et al., "The Relative Affinities of Coordinating Atoms for Silver Ion, Part II, Nitrogen, Phosphorous and Arsenic", J. Chem. Soc., pp. 276-288, (1958).

Primary Examiner—Helen M. S. Sneed
Attorney, Agent, or Firm—Deane E. Keith; Forrest D. Stine; Joseph J. Carducci

[57] ABSTRACT

There are provided novel Group VA ylides defined by the following Formula I:

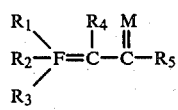

wherein $R_1$, $R_2$, $R_3$, $R_4$ and $R_5$ are either alike or different members selected from the group consisting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbon atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hydroxyl group; an alkoxy or aryloxy group; a hydrocarbyl group, such as defined above, carrying halogen, hydroxyl, alkoxy or aryloxy; and a sulfonato group ($-SO_3^-$) or an alkyl, aryl, alkenyl, cycloalkyl, aralkyl or alkaryl group carrying a sulfonato group; provided that at least one of $R_1$, $R_2$ and $R_3$ is a sulfonato group or an alkyl, aryl, alkenyl, cycloalkyl, aralkyl or alkaryl, as defined above, carrying a sulfonato group; M is sulfur or oxygen, preferably oxygen; and F is phosphorus, arsenic or antimony, preferably phosphorus.

The process for preparing these Group VA ylides comprises reacting a ligand defined by the following formula:

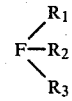

with an alpha-substituted ketone or aldehyde or an alpha-substituted thioketone or thioaldehyde defined by the following formula:

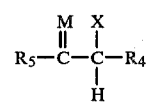

to obtain the salt defined by the following Formula II:

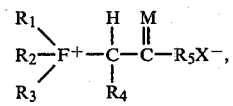

wherein $R_1$, $R_2$, $R_3$, $R_4$, $R_5$, F and M are as defined above and X is a halogen radical selected from the group consisting of fluorine, chlorine, bromine and iodine, preferably chlorine and bromine, a tosyl group (a toluene sulfonate group), or an acetate group. This salt is reacted with a base to obtain the novel ylide defined by Formula I.

25 Claims, No Drawings

GROUP VA YLIDES AND PROCESS FOR PREPARING SAME

CROSS-REFERENCES TO RELATED APPLICATIONS

This application is a continuation-in-part of our U.S. patent application Ser. No. 179,079, filed Aug. 18, 1980, now U.S. Pat. No. 4,293,502 entitled "Nickel Ylides"; U.S. patent application Ser. No. 179,080, filed Aug. 18, 1980, entitled "Process for the Preparation of Nickel Ylides Containing Ylide Ligands With a Sulfonated Group V Component"; U.S. patent application Ser. No. 179,076, filed Aug. 18, 1980, now U.S. Pat. No. 4,293,727 entitled "Process for the Oligomerization of Ethylene"; and U.S. patent application Ser. No. 179,005, filed Aug. 18, 1980, now U.S. Pat. No. 4,310,716 entitled "Process for the Oligomerization of Ethylene in Methanol".

Reference is made to applicants' following U.S. applications:

U.S. patent application Ser. No. 210,413, filed Nov. 25, 1980, now U.S. Pat. No. 4,301,318 entitled "Process for Recovering Oligomerization Product".

U.S. patent application Ser. No. 209,673, filed Nov. 24, 1980, entitled "Novel Group VA Salts and Process for Preparing Same."

U.S. patent application Ser. No. 209,674, filed Nov. 24, 1980, entitled "Sulfonated Group VA Ylides and Process for Preparing Same".

The disclosures of the foregoing applications are hereby incorporated by reference.

FIELD OF THE INVENTION

The present invention relates to novel Group VA ylides which are useful in the preparation of nickel ylide catalysts for the oligomerization of ethylene. This invention also relates to a process for preparing such Group VA ylides.

DESCRIPTION OF THE PRIOR ART

It is well known in the art to use a variety of catalysts to oligomerize ethylene to higher molecular weight olefins. The term "oligomerize" has been employed, and is employed herein to describe the conversion of lower olefins such as ethylene to olefinic products of higher molecular weight, e.g., to dimer, trimer, tetramer and the like. The reaction rate and product distribution obtained are highly dependent on the exact catalyst composition and the reaction conditions employed. Two such general classes of catalysts are the "Ziegler" types consisting of aluminum trialkyls and the "Ziegler-Natta" types consisting of aluminum alkyls or alkyl halides and titanium halides. Major disadvantages of aluminum alkyl catalysts are their highly reactive and pyrophoric nature and the fact that they must be used at relatively high temperatures, e.g., 200°-275° C. and pressures, e.g., 2000-4000 psig (13,790 to 27,580 kPa). Although much milder reaction conditions are used when the aluminum alkyls are used in conjunction with titanium halides, product quality and ease of catalyst separation from products of both of these prior art types of catalysts are not as high as desired.

An article by W. Keim, F. H. Kowaldt, R. Goddard and C. Kruger entitled "Novel Coordination of (Benzoylmethylene)triphenylphosphorane in a Nickel Oligomerization Catalyst", in *Angew. Chem. Int. Ed. Engl.* (1978) No. 6, page 466, discloses the preparation of a nickel ylide by the following reaction:

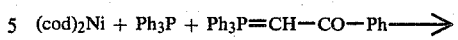

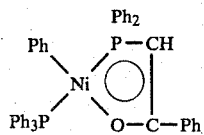

wherein "cod" represents 1,5-cyclooctadiene and "Ph" represents phenyl. It is reported that the resultant nickel ylide converts ethylene into alpha olefins or polyethylene.

Ahrland et al in an article entitled "The Relative Affinities of Coordinating Atoms for Silver Ion. Part II, Nitrogen, Phosphorous and Arsenic", in *J. Chem. Soc.* (1958) pages 276–288, disclose the sulfonation of triphenylphosphine in fuming sulfuric acid. The product, sodium diphenylphosphinobenzene-3-sulfonate, has the following structure:

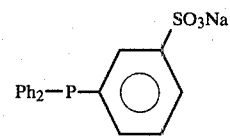

wherein "Ph" represents phenyl.

SUMMARY OF THE INVENTION

The novel Group VA ylides of this invention are defined by the following Formula I:

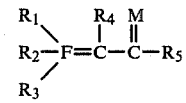

wherein $R_1$, $R_2$, $R_3$, $R_4$ and $R_5$ are either alike or different members selected from the group consisting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbons atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hydroxyl group; an alkoxy or aryloxy group; a hydrocarbyl group, such as defined above, carrying halogen, hydroxyl, alkoxy or aryloxy; and a sulfonato group ($-SO_3^-$) or an alkyl, aryl, alkenyl, cycloalkyl, aralkyl or alkaryl group carrying a sulfonato group; provided that at least one of $R_1$, $R_2$ and $R_3$ is a sulfonato group or an alkyl, aryl, alkenyl, cycloalkyl, aralkyl or alkaryl, as defined above, carrying a sulfonato group; M is sulfur or oxygen, preferably oxygen; and F is phosphorus, arsenic or antimony, preferably phosphorus.

The process for preparing the novel Group VA ylides of this invention comprises reacting a ligand defined by the following formula:

with an alpha-substituted ketone or aldehyde or an alpha-substituted thioketone or thioaldehyde defined by the following formula:

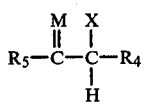

to obtain the Group VA salt defined by the following Formula II:

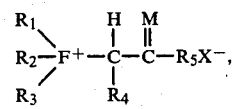

wherein $R_1$, $R_2$, $R_3$, $R_4$, $R_5$, F and M are as defined above and X is a halogen radical selected from the group consisting of fluorine, chlorine, bromine and iodine, preferably chlorine and bromine, a tosyl group (a toluene sulfonate group), or an acetate group. This Group VA salt is reacted with a base to obtain the novel ylide defined by Formula I.

DESCRIPTION OF THE PREFERRED EMBODIMENTS

To prepare the Group VA ylides of this invention, a ligand defined by the formula:

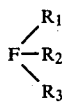

wherein $R_1$, $R_2$, $R_3$ and F are as defined above, is reacted with an alpha substituted ketone or aldehyde or an alpha substituted thioketone or thioaldehyde defined by the following formula:

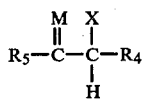

wherein $R_4$, $R_5$, M and X are as defined above. The sulfonated ligand can be obtained in any conventional manner by sulfonating the appropriate trihydrocarbyl phosphine, arsine or stibine, e.g., by sulfonating using $SO_3$ in the presence of a strong inorganic mineral acid, such as sulfuric acid, hydrochloric acid, nitric acid, phosphoric acid, etc. It is preferred to use fuming sulfuric acid ($H_2SO_4 \cdot x\ SO_3$, where x can be, for example, from about 0.1 to about 0.6, preferably from about 0.2 to about 0.4). The amount of $SO_3$ is not critical and can vary over a wide range, for example, at least about one mole per mole of ligand, preferably from about two to about 20 moles per mole of ligand. The two reactants are stirred and heated at a temperature of about 0° to about 200° C., preferably about 40° to about 100° C., for about one minute to about 48 hours, preferably for about 30 minutes to about four hours. Any suitable pressure can be used, although atmospheric pressure is preferred. At the end of this period the reactor contents are cooled to a temperature of about −30° to about 50° C., preferably about room temperature (about 26° C.), after which sufficient water and a suitable base, such as an alkaline metal hydroxide, an alkali metal alkoxide, ammonium hydroxide, a hydrocarbyl-substituted ammonium hydroxide, etc. are added thereto to crystallize the sulfonated ligand out of solution. For example, the amount of water used can range from about 10 milliliters to about 10 liters per mole of sulfonated ligand. The crystals can be recovered in any suitable manner, for example, by filtration, decantation or by centrifuging. Specific examples of ligands that can be used include: allyldiphenylphosphine; benzyldiphenylphosphine; bis(3-aminopropyl)phenylphosphine; bis(2-cyanoethyl)phenylphosphine; bis(m-fluorophenyl)-phosphinous chloride; 4-bromophenyldiphenylphosphine; n-butyldiphenylphosphine; t-butyldiphenylphosphine; 2-cyanoethyldiphenylphosphine; cyclohexyldiphenylphosphine; n-decylphenylphosphine; diallylphenylphosphine; di-n-amylphenylphosphine; di-sec-butylphenylphosphine; dicyclohexylphenylphosphine; diethylphenylphosphine; di-n-heptylphenylphosphine; di-n-hexylphenylphosphine; dimethylphenylphosphine; dimethyl-p-tolylphosphine; diphenyl-n-butoxyphosphine; diphenylchlorophosphine; diphenylenephenylphosphine; diphenylethoxyphosphine; diphenylmethoxyphosphine; diphenylphosphine; beta-diphenylphosphinoethyltriethoxysilane; di-isopropylphenylphosphine; di-o-tolylphenylphosphine; divinylphenylphosphine; ethyldiphenylphosphine; n-hexyldiphenylphosphine; o-methoxyphenyldiphenylphosphine; (2-methylbutyl)diphenylphosphine; methyldiphenylphosphine; methylethylphenylphosphine; methylphenylphosphine; neomenthyldiphenylphosphine; pentafluorophenyldiphenylphosphine; (2-phenylbutyl)diphenylphosphine; phenyldi-n-butoxyphosphine; phenyldichlorophosphine; phenyldiethoxyphosphine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris(m-chlorophenyl)phosphine; tris(p-chlorophenyl)phosphine; tri(1-naphthyl)phosphine; triphenylphosphine; tris(4-dimethylaminophenyl)phosphine; tris(p-fluorophenyl)phosphine; tris(o-methoxyphenyl)phosphine; tris(p-methoxyphenyl)phosphine; tri-o-tolylphosphine; tri-m-tolylphosphine; tri-p-tolylphosphine; vinyldiphenylphosphine; sodium diphenylphosphinebenzene-3-sulfonate; disodium phenylphosphinebis(benzene-3-sulfonate); dimethylphenylarsine; methyldiphenylarsine; triphenylarsine; tri-p-tolylarsine; diphenylchloroarsine; and triphenylantimony. Specific examples of such alpha substituted ketones or aldehydes and of alpha substituted thioketones or thioaldehydes that can be used herein include: phenacylchloride; phenacylbromide; alpha-acetoxyacetophenone; alpha-bromo-2'-acetonaphthone; alpha-bromoacetone; 3-bromocamphor; alpha-bromo-p-chloroacetophenone; alpha-bromo-2',4'-dimethoxyacetophenone; alpha-bromoiosbutyrophenone; alpha-bromo-o-methoxyacetophenone; alpha-bromo-m-methoxyacetophenone; alpha-bromo-p-methoxyacetophenone; alpha-bromo-4'-methylacetophenone; p-bromophenacylbromide; alpha-bromopropiophenone; chloroacetone; alpha-chloro-p-fluoroacetophenone; alpha-chlorobutyrophenone; p-chlorophenacylchloride; alpha-chloropropiophenone; alpha-chlorothioacetophenone; alpha-bromothioacetophenone; alpha-chloroethylnaphthylketone; alpha-chloromethylacetate; alpha-bromomethylacetate; alpha-chloroethylacetate; alpha-bromoethylacetate; alpha-chloropropylacetate; alpha-chlorobutylacetate; alpha-chlorophenylacetate; alpha-chloro-p-sulfonatophenylacetate; alpha-bromopropylacetate; alpha-bromobutylacetate; alpha-bromophenylacetate; and alpha-bromo-p-sulfonatophenylacetate.

The reaction between the sulfonated ligand and the ketone or aldehyde is carried out using about equal molar amounts of each reactant while they dissolved in an appropriate hydrocarbon solvent, such as toluene or tetrahydrofuran, and the reaction is carried out at a temperature of about 20° to about 200° C., preferably about 50° to about 150° C., and any suitable pressure, preferably atmospheric, for about one to about 24 hours, preferably for about two to about eight hours. The reaction mixture is then cooled, preferably to room temperature. If a solid results from such cooling it is recovered in any suitable manner, for example, by filtration, decantation or by centrifuging. If solids do not form, the reaction mixture can be subjected to distillation to remove solvents therefrom, leaving behind novel solid material, which is a salt defined by the following Formula II.

$$\begin{array}{c} R_1 \\ \phantom{R_2-}\diagdown \\ R_2-F^+-\overset{R_4}{\underset{H}{C}}-\overset{M}{\overset{\|}{C}}-R_5 \quad X^- \\ \phantom{R_2-}\diagup \\ R_3 \end{array}$$

wherein $R_1$, $R_2$, $R_3$, $R_4$, $R_5$, F, M and X are as defined above.

To convert the above salt to the corresponding ylide, the salt is reacted with a stoichiometric amount of a base, such as an alkali metal hydroxide (sodium or potassium hydroxide), an alkyl or aryl lithium (n-butyl lithium, methyl lithium or phenyl lithium), an alkoxide (sodium methoxide or potassium t-butoxide), a hydrocarbyl-substituted ammonium hydroxide (benzyltrimethylammonium hydroxide), ammonium hydroxide, ammonia, etc. This can be done, for example, by suspending or dissolving the salt in a suitable liquid, such as water, an alcohol (ethanol or isopropanol), an aromatic (benzene or toluene), a hydrocarbon (hexane or heptane), etc. The reaction temperature can range from about room temperature to about 200° C., preferably from about room temperature to about 50° C., and the reaction time from about one minute to about four hours, or even longer, but preferably from about one to about two hours. Elevated pressures can be used, although atmospheric pressure will suffice. If the ylide obtained is a solid, recovery can be effected by filtration, decantation or by centrifuging. If the ylide is dissolved in the solvent, simple distillation is sufficient to remove the solvent, leaving behind the solid ylide. In some cases in association with the ylide so recovered will be the salt corresponding to the base that was used. For example, use of sodium hydroxide produces the corresponding sodium salt. The salt and the desired ylide can be separated from each other in any convenient manner, for example, by extraction with a solvent that will dissolve one and not the other. For example, aromatics, such as toluene, can be used to dissolve the ylide, while water can be used to dissolve the salt. The novel ylide obtained can be defined by the following Formula I:

$$\begin{array}{c} R_1 \\ \phantom{R_2-}\diagdown \\ R_2-F=\overset{R_4}{\underset{}{C}}-\overset{M}{\overset{\|}{C}}-R_5 \\ \phantom{R_2-}\diagup \\ R_3 \end{array}$$

wherein $R_1$, $R_2$, $R_3$, $R_4$, $R_5$, F and M are as defined above.

Specific examples of Group VA ylides defined by Formula I which can be prepared in accordance with this invention are set forth in Table I. In this table and as used elsewhere herein, "Ph" represents phenyl.

TABLE I

| Compound | $R_1$ | $R_2$ | $R_3$ | $R_4$ | $R_5$ | F | M |
|---|---|---|---|---|---|---|---|
| 1 | Ph | Ph | 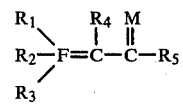 | H | Ph | P | O |
| 2 | 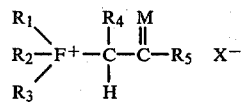 | Ph | Ph | H | Ph | P | O |
| 3 | 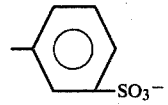 | Ph | Ph | H | Ph | P | O |
| 4 | Ph | 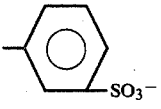 | Ph | H | OCH$_3$ | P | O |

TABLE I-continued

| Compound | R₁ | R₂ | R₃ | R₄ | R₅ | F | M |
|---|---|---|---|---|---|---|---|
| 5 | Ph | CH₃ | -C₆H₄-SO₃⁻ | H | OC₄H₉ | P | S |
| 6 | Ph | -C₆H₄-SO₃⁻ | Ph | SO₃⁻ | -O-C₆H₄-SO₃⁻ | P | O |
| 7 | Ph | -C₆H₄-SO₃⁻ | Ph | H | CH₃ | As | O |
| 8 | Ph | -C₆H₄-SO₃⁻ | Ph | H | -C₆H₄-OCH₃ | P | O |

The novel ylides of this invention are useful in the preparation of nickel ylide catalysts defined by the following Formula III:

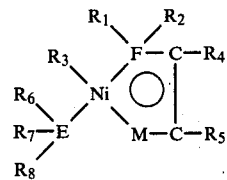

wherein $R_1$, $R_2$, $R_3$, $R_4$, $R_5$, F and M are as defined above; $R_6$, $R_7$ and $R_8$ can be the same as previously defined for $R_1$, $R_2$, $R_3$, $R_4$ and $R_5$; and E is phosphorous, arsenic, antimony or nitrogen, preferably phosphorus. To prepare the nickel ylide catalyst defined by Formula III, the Group VA ylide of this invention is reacted with (1) a ligand defined by the formula:

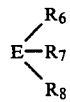

wherein $R_6$, $R_7$, $R_8$ and E are as defined above; and (2) a zero valent nickel compound or any nickel compound convertible to a zero valent nickel compound in situ. Specific examples of ligands that can be used include: allyldiphenylphosphine; benzyldiphenylphosphine; bis(3-aminopropyl)phenylphosphine; bis(2-cyanoethyl)phenylphosphine; bis-(m-fluorophenyl)phosphinous chloride; 4-bromophenyldiphenylphosphine; n-butyldiphenylphosphine; t-butyldiphenylphosphine; 2-cyanoethyldiphenylphosphine; cyclohexyldiphenylphosphine; n-decylphenylphosphine; diallylphenylphosphine; di-n-amylphenylphosphine; di-sec-butylphenylphosphine; dicyclohexylphenylphosphine; diethylphenylphosphine; di-n-heptylphenylphosphine; di-n-hexylphenylphosphine; di-methylphenylphosphine; dimethyl-p-tolylphosphine; di-phenyl-n-butoxyphosphine; diphenylchlorophosphine; diphenylenephenylphosphine; diphenylethoxyphosphine; diphenylmethoxyphosphine; diphenylphosphine; beta-diphenylphosphinoethyltriethoxysilane; di-iso-propylphenylphosphine; di-o-tolylphenylphosphine; divinylphenylphosphine; ethyldiphenylphosphine; n-hexyldiphenylphosphine; o-methoxyphenyldiphenylphosphine; (2-methylbutyl)diphenylphosphine; methyldiphenylphosphine; methylethylphenylphosphine; methylphenylphosphine; neomenthyldiphenylphosphine; pentafluorophenyldiphenylphosphine; (2-phenylbutyl)diphenylphosphine; phenyldi-n-butoxyphosphine; phenyldichlorophosphine; phenyldiethoxyphosphine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris(m-chlorophenyl)phosphine; tris(p-chlorophenyl)phosphine; tri(1-naphthyl)phosphine; triphenylphosphine; tris(4-dimethylaminophenyl)phosphine; tris(p-fluorophenyl)phosphine; tris(o-methoxyphenyl)phosphine; tris(p-methoxyphenyl)phosphine; tri-o-tolylphosphine; tri-m-tolylphosphine; tri-p-tolylphosphine; vinyldiphenylphosphine; sodium diphenylphosphinebenzene-3-sulfonate; disodium phenylphosphine-bis(benzene-3-sulfonate); dimethylphenylarsine; methyldiphenylarsine; triphenylarsine; tri-p-tolylarsine; diphenylchloroarsine; triphenylantimony; triphenylamine; tribenzylamine; methyldiphenylamine; dimethylphenylamine; bis(2-cyanoethyl)phosphine; bis(dimethylamino)methylphosphine; t-butyldichlorophosphine; 2-cyanoethylphosphine; cyclohexylphosphine; di-t-butylchlorophosphine; dicyclohexylphosphine; diethylethoxyphosphine; diethyl-iso-propoxyphosphine; diethylphosphine; triallylphosphine; tri-iso-butylphosphine; tri-n-butylphosphine; tri-sec-butylphosphine; tri-t-butylphosphine; triethylphosphine; tri-n-hexylphosphine; trimethylphosphine; trifluorophosphine; tri-iso-propylphosphine; tri-n-propylphosphine; tris(2-cyanoethyl)phosphine; tris(dimethylamino)phosphine; tris-(trimethylsilyl)phosphine; tri-n-butylantimony; triethylarsine; trimethylarsine; methyldiiodoarsine; trimethylamine; triethylamine; tributylamine; tripropylamine; di-methylamine; di-n-hexylamine; dicyclohexylamine; diethylamine; tricyclohexylamine; ammonia, and phosphine. Specific examples of nickel compounds which can be used include: tris(triphenylphosphine)nickel; bis(cyclooctadiene)nickel; tetrakis(triphenylphosphine)nickel; bis(norbornadiene)-nickel; (cyclooctа-1,5-diene)duroquinone nickel; (dicyclopentadiene)duroquinone nickel; bis(tetracyclone)nickel; tetrakis(triethylphosphine)nickel; tris(triethylphosphine)nickel; bis(triphenylphosphine)nickel dicarbonyl; nickel carbonyl; nickel(II)acetylacetonate; nickelocene; bis(triethylphosphine)nickel(II)chloride; tetrakis(tri-fluorophosphine)nickel; nickel acetate; nickel bromide; nickel carbonate; nickel chloride; nickel fluoride; nickel iodide; nickel nitrate; nickel sulfate; nickel 2,4-pentanedionate; bis π-allyl nickel; and nickel dichloride hexaamine.

In this step, approximately equal molar amounts of each of the three reactants defined above are dissolved in any suitable unreactive solvent, such as toluene, tetrahydrofuran, dioxane, or other unreactive hydrocarbon solvents, and stirred while maintaining a temperature of about 0° to about 100° C., preferably room temperature, for about one-half hour to about 48 hours, preferably about three to about 20 hours, sufficient to ensure complete reaction. Any suitable pressure can be used, although atmospheric pressure is preferred. The solvent can be removed from the reaction mixture in any suitable manner, for example, by distillation, including vacuum distillation, if necessary, leaving behind the novel compound defined above. On the other hand, a second solvent in which the desired product is insoluble, such as heptane, can be added to the reaction product to precipitate the novel compound therein. The novel compound can be recovered, for example, by filtration, decantation or by centrifuging.

The following examples illustrate the invention, and are not intended to limit the invention, but rather, are presented for purposes of illustration. Example I illustrates the preparation of a Group VA ylide of this invention; Example II illustrates the use of this Group VA ylide in the preparation of a nickel ylide; and Example III illustrates the use of this nickel ylide to oligomerize ethylene.

EXAMPLE I

To 20 milliliters of 30 percent fuming sulfuric acid there were added slowly with cooling 10 grams of triphenylphosphine. The solution was then heated to 80° C. and every five minutes the solution was tested by adding one drop of the solution to water until a clear solution was obtained. The reaction mixture was cooled to room temperature, poured into 200 cc of water and neutralized with 10 percent aqueous sodium hydroxide. After setting the solution overnight at room temperature, the desired product separated by crystallization and was recovered by filtration. The recovered product, sodium diphenylphosphinobenzene-3-sulfonate has the following structure:

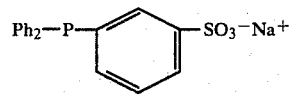

(Compound 1)

To 4.65 grams of alpha-chloroacetophenone (0.03 mole) in 150 milliliters of toluene there were added 10.92 grams of sodium diphenylphosphinobenzene-3-sulfonate (0.03 mole). This was heated to reflux under argon for five hours and then cooled and filtered. A total of 14.52 grams of the novel phosphonium salt:

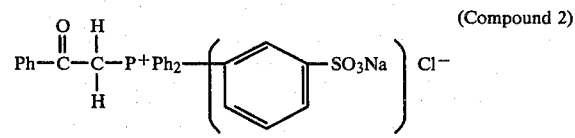

(Compound 2)

was obtained which was suspended in ethanol/water and titrated with 10 percent sodium hydroxide to a phenolphthalein end point. The ethanol was removed in vacuo and the product was washed with toluene to remove a small amount of unsubstituted benzoylmethylene triphenylphosphorane (1.2 grams). A total of 12.89 grams of the following novel phosphonium compound:

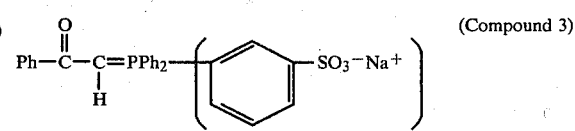

(Compound 3)

was obtained in 89 percent yield.

EXAMPLE II

To 1.38 grams of bis(cyclooctadiene)nickel (five millimoles) in 70 milliliters of tetrahydrofuran there was added a mixture of 1.31 grams of triphenylphosphine (five millimoles) and 2.41 grams of Compound 3 (five millimoles) dissolved in 70 milliliters of tetrahydrofuran. This was stirred at room temperature for 18 hours, after which the solvent was removed in vacuo. The resulting product was dissolved in toluene and filtered. Heptane was then added to precipitate the following novel nickel ylide:

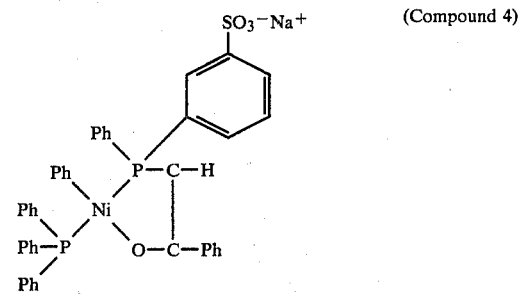

(Compound 4)

EXAMPLE III

A run was carried out wherein there was charged 0.1 millimole of the sulfonated nickel ylide catalyst obtained in Example II, Compound 4, dissolved in 100 milliliters of toluene. During the reaction precautions were taken to exclude air contamination by performing the reaction in an argon atmosphere. The reaction mixture was then heated to 50° C. and pressured with ethylene to obtain a partial pressure thereof of 200 pounds per square inch gauge (1400 kPa). The reaction mixture was stirred throughout the reaction period of two hours, during which time the temperature and pressure was maintained constant. At the end of the two-hour period the reaction mixture was cooled to room temperature and unreacted ethylene removed therefrom by distillation. The amount of oligomer produced was determined and compared with the activity for the compound reported by the Keim et al article previously discussed. The results obtained are set forth in Table II.

TABLE II

| Run No. | Nickel Ylide Catalyst | Activity: Moles Ethylene Converted Per Mole of Nickel Catalyst |
|---|---|---|
| I | Keim et al specific catalyst | 6,000* |
| II | Compound 4 | 6,965 |

*Reported by Keim et al

Compound 4 is more active than the unsulfonated nickel ylide of Keim et al. An additional advantage of Compound 4 over that of Keim et al lies in its easy recovery from the reaction product.

Although the invention has been described in considerable detail with particular reference to certain preferred embodiments thereof, variations and modifications can be effected within the spirit and scope of the invention as described hereinbefore, and as defined in the appended claims.

We claim:

1. A Group VA ylide defined by the following formula:

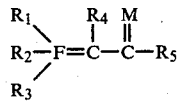

wherein $R_1$, $R_2$, $R_3$, $R_4$ and $R_5$ are either alike or different members selected from the group consisting of hydrogen, alkyl radicals having from about one to about 24 carbon atoms, aryl radicals having from about six to about 20 carbon atoms, alkenyl radicals having from about two to about 30 carbon atoms, cycloalkyl radicals having from about three to about 40 carbon atoms, aralkyl and alkaryl radicals having from about six to about 40 carbon atoms, hydrocarbyl groups carrying halogen, hydroxyl, alkoxy or aryloxy, or an alkyl, aryl, alkenyl, cycloalkyl, aralkyl or alkaryl group carrying a sulfonato group, provided that at least one of $R_1$, $R_2$ and $R_3$ is an alkyl, aryl, alkenyl, cycloalkyl, alkaryl or aralkyl carrying a sulfonato group; M is sulfur or oxygen; F is phosphorus, arsenic or antimony; and further provided that F is bonded to the groups $R_1$, $R_2$ and $R_3$ through carbon.

2. An ylide as defined in claim 1 wherein F is phosphorus and M is oxygen.

3. An ylide as defined in claim 1 wherein each of $R_1$, $R_2$ and $R_3$ is phenyl, one of which is substituted with a sulfonato group.

4. An ylide as defined in claim 2 wherein each of $R_1$, $R_2$ and $R_3$ is phenyl, one of which is substituted with a sulfonato group.

5. An ylide as defined in claim 1 wherein $R_4$ is hydrogen and $R_5$ is phenyl.

6. An ylide as defined in claim 2 wherein $R_4$ is hydrogen and $R_5$ is phenyl.

7. An ylide as defined in claim 3 wherein $R_4$ is hydrogen and $R_5$ is phenyl.

8. An ylide as defined in claim 4 wherein $R_4$ is hydrogen and $R_5$ is phenyl.

9. A process for preparing a Group VA ylide defined by the following formula:

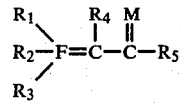

which comprises reacting a ligand defined by the following formula:

with an alpha-substituted ketone or aldehyde or an alpha-substituted thioketone or thioaldehyde defined by the following formula:

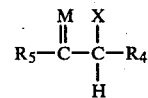

to obtain the salt defined by the following formula:

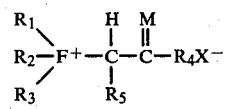

and thereafter reacting the salt so obtained with a base, wherein $R_1$, $R_2$, $R_3$, $R_4$ and $R_5$ are either alike or different members selected from the group consisting of hydrogen, alkyl radicals having from about one to about 24 carbon atoms, aryl radicals having from abut six to about 20 carbon atoms, alkenyl radicals having from about two to about 30 carbon atoms, cycloalkyl radicals having from about three to about 40 carbon atoms, aralkyl and alkaryl radicals having from about six to about 40 carbon atoms, hydrocarbyl groups carrying halogen, hydroxyl, alkoxy or aryloxy, or an alkyl, aryl, alkenyl, cycloalkyl, aralkyl or alkaryl group carrying a sulfonato group, provided that at least one of $R_1$, $R_2$ and $R_3$ is an alkyl, aryl, alkenyl, cycloalkyl, alkaryl or aralkyl carrying a sulfonato group; M is sulfur or oxygen; F is phosphorus, arsenic or antimony; X is a halogen radical, a tosyl group or an acetate group; and further provided that F is bonded to the groups $R_1$, $R_2$ and $R_3$ through carbon.

10. A process as defined in claim 9 wherein E and F are both phosphorus and M is oxygen.

11. A process as defined in claim 9 wherein each of $R_1$, $R_2$ and $R_3$ is phenyl, one of which is substituted with a sulfonato group.

12. A process as defined in claim 10 wherein each of $R_1$, $R_2$ and $R_3$ is phenyl, one of which is substituted with a sulfonato group.

13. A process as defined in claim 9 wherein $R_4$ is hydrogen and $R_5$ is phenyl.

14. A process as defined in claim 10 wherein $R_4$ is hydrogen and $R_5$ is phenyl.

15. A process as defined in claim 11 wherein $R_4$ is hydrogen and $R_5$ is phenyl.

16. A process as defined in claim 12 wherein $R_4$ is hydrogen and $R_5$ is phenyl.

17. A process as defined in claim 16 wherein X is chlorine.

18. A process as defined in claim 9 wherein the reaction between the ligand and the ketone or aldehyde is carried out at a temperature of about 20° to about 200° C. for about one to about 24 hours.

19. A process as defined in claim 9 wherein the reaction between the ligand and the ketone or aldehyde is carried out at a temperature of about 50° to about 150° C. for about two to about eight hours.

20. A process as defined in claim 17 wherein the reaction between the ligand and the ketone or aldehyde is carried out at a temperature of about 20° to about 200° C. for about one to about 24 hours.

21. A process as defined in claim 17 wherein the reaction between the ligand and the ketone or aldehyde is carried out at a temperature of about 50° to about 150° C. for about two to about eight hours.

22. A process as defined in claim 9 wherein said salt is converted to the corresponding ylide by reacting with a base at a temperature of from about room temperature to about 200° C. for about one minute to about four hours.

23. A process as defined in claim 9 wherein said salt is converted to the corresponding ylide by reacting with a base at a temperature of from about room temperature to about 50° C. for about one to about two hours.

24. A process as defined in claim 17 wherein said salt is converted to the corresponding ylide by reacting with a base at a temperature of from about room temperature to about 200° C. for about one minute to about four hours.

25. A process as defined in claim 17 wherein said salt is converted to the corresponding ylide by reacting with a base at a temperature of from about room temperature to about 50° C. for about one to about two hours.

* * * * *